United States Patent [19]

Lolachi et al.

[11] 4,187,846
[45] Feb. 12, 1980

[54] STERILE CONNECTORS

[75] Inventors: Houshang Lolachi, Westport, Conn.; Robert N. Carminucci, Purdy, N.Y.

[73] Assignee: Union Carbide Corporation, New York, N.Y.

[21] Appl. No.: 918,025

[22] Filed: Jun. 22, 1978

[51] Int. Cl.² .............................................. A61M 05/00
[52] U.S. Cl. ..................................... 128/214 R; 285/3; 285/352; 285/423
[58] Field of Search ................. 285/352, 423, DIG. 2, 285/260, 332, 3, 4; 128/214 R, 214.2

[56] References Cited

U.S. PATENT DOCUMENTS

| | | | |
|---|---|---|---|
| 3,052,489 | 9/1962 | Stoudt | 285/352 X |
| 3,865,411 | 2/1975 | Rowe et al. | 285/363 |
| 3,986,508 | 10/1976 | Barrington | 128/214.2 |
| 4,019,512 | 4/1977 | Tenczar | 128/214 R |
| 4,022,205 | 5/1977 | Tenczar | 128/214 R |
| 4,030,494 | 6/1977 | Tenczar | 128/214 R |

Primary Examiner—Thomas F. Callaghan
Attorney, Agent, or Firm—Alvin H. Fritschler

[57] ABSTRACT

The interior sections of companion sterile connector members are isolated from the atmosphere by shield plates that are movable to uncover aligned conduits in said members through which luer fitting sections are engaged. Compressible seals positioned intermediate said shield plates and said connector members expand and contact one another as the shield plates are moved, thus forming a seal-line that advances behind the trailing edge of the shield plates as the plates are moved to uncover said conduits. The seals thus preserve the sterility of the connector prior to engagement of the luer fittings and provide added assurance against contamination thereafter without contact with the fluid passing through the luer fittings within the connector. In various embodiments, the shield plates are conveniently slid or rotated from the closed to the open position. Sterility protection is further assured by utilizing seals containing cavities forming thin membrane sections penetrable by the luer fitting and positioned in alignment with said connector member conduits.

24 Claims, 9 Drawing Figures

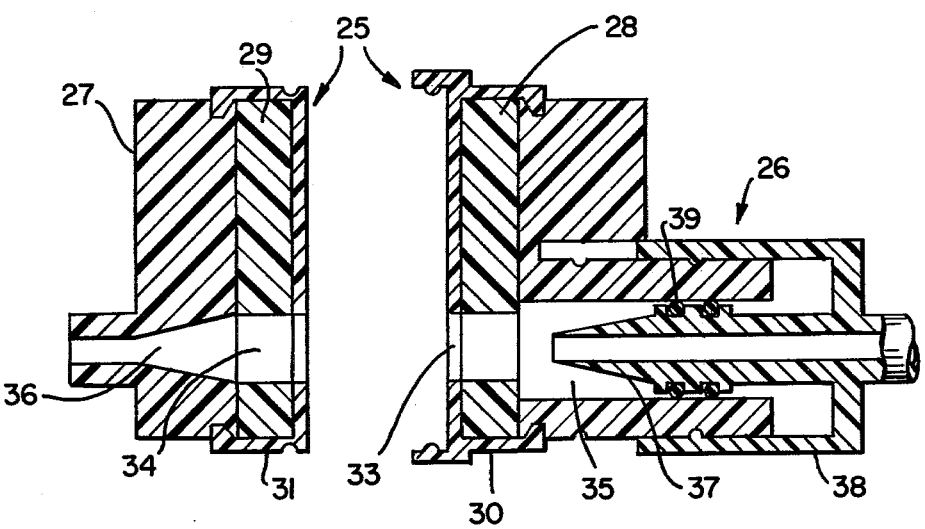
FIG. 5
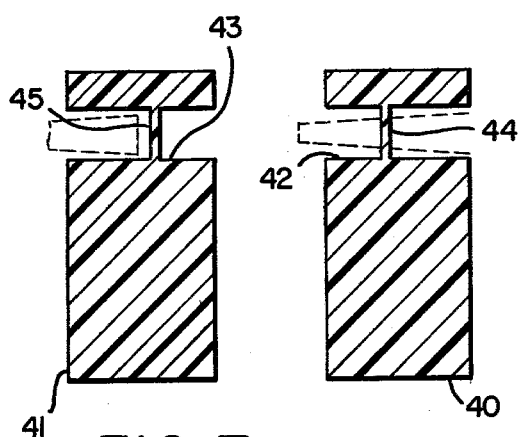
FIG. 7
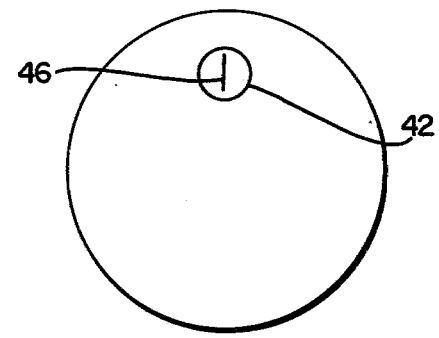
FIG. 8
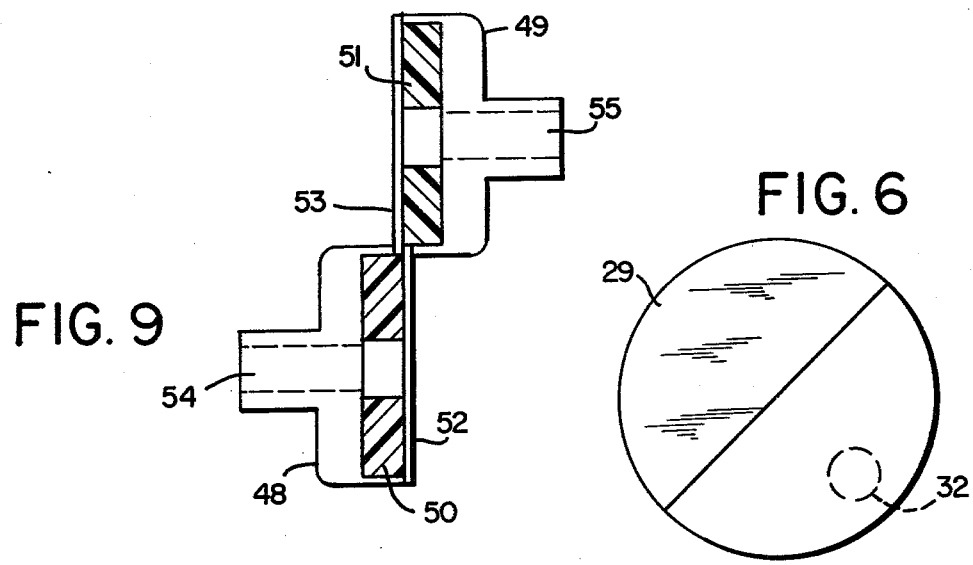
FIG. 9
FIG. 6

STERILE CONNECTORS

BACKGROUND OF THE INVENTION

1. Field of the Invention

The invention relates to a sterile connector assembly. More particularly, it relates to a sterile connector having enhanced protection of blood or other fluids against environmental contamination.

2. Description of the Prior Art

Various sterile docketing devices, or sterile connectors, have been proposed in the art. Such devices have not generally been satisfactory for commercial applications, however, because of various problems associated with the design and handling characteristics of such connectors. In one approach, for example, heat supplied by an external source must be applied to the area being mated by the two parts of the connector. In another approach, a thin film of folded material is employed to cover and isolate each of the sterilized connector parts. After the parts have been locked together, the films may be pulled, as by means of thin U-shaped tabs thereon, so as to remove the films in such a way that only the sterile surfaces of the connector parts are in contact, elastomeric seals behind the films being released and joined from both sides to maintain the sterile environment. Film thickness is a problem in this approach, as a very thin film may not withstand the force of the pulling action while a thicker film is subject to folding difficulties.

In the latter approach, the folding line is always at least twice the thickness of the film, resulting in a potential for contamination as the film is removed. The film and seal arrangement is also incapable of withstanding any measurable pressure, such as those of autoclaving and centrifugal pressures. In addition to the adherence of the elastomeric seals to the connector body parts, the films are sealed to said elastomeric material, thus introducing adhesion problems and potential contamination to the compressible interface.

A genuine need exists, therefore, for a practical sterile connector capable of achieving enhanced sterility protection while providing simplified operating characteristics and adaptability to the conditions under which such connectors would be employed in the processing of blood and other fluids. In medical and particularly in blood transfusion fields, connections between bags and tubes to establish fluid flow paths must be made without exposing the interior of the coupling connectors to contamination by air or through infection by microorganisms. Because of existing limitations associated with the presently available means of connection, the post thaw period in blood freezing and washing operations, and in the field of blood component separation, is presently limited to a 24-hour outdating period. This limitation constitutes a severe restriction that is a major concern to blood processing agencies confronted with the proper utilization of available blood supplies, particularly when the need for such supplies becomes acute as during emergency situations. The development of a sterile connector has been recognized as a key to the alieviating of such problems as by the highly desirable extension of said post thaw period beyond the present 24-hour period.

It is an object of the invention, therefore, to provide a practical sterile connector.

It is another object of the invention to provide a sterile connector having enhanced sterility protection.

It is another object of the invention to provide a sterile connector having convenient operating characteristics for practical connector applications.

It is a further object of the invention to provide sterile connectors having simplified operating capability coupled with enhanced assurance against contamination of blood or other fluids passing through said connectors.

SUMMARY OF THE INVENTION

The objects of the invention are accomplished by employing a sterile connector having shield plates that are slidable, rotatable or otherwise movable so as to uncover aligned conduits in matingly engaged male and female connector members through which companion luer fitting sections are engaged. Compressible seals intermediate the connector members and said shield plates are released as the shield plates are moved from a closed to an open position, thereby expanding and contacting each other, thus forming a seal-line that advances behind the trailing edge of the shield plates as said plates are moved to uncover said conduits. The seals thereby preserve the sterile environment within the connector until the luer fittings are engaged and provide an added assurance against contamination thereafter. The seals, which are not exposed to contact by the fluid passing through the luer fittings within the connector, may be provided in various shapes and configurations with the sterility of the connector being further assured by utilizing seals having cavities therein forming recessed thin membrane sections in alignment with the conduits in the male and female connector members of the sterile connector assembly and penetrable by said luer fittings.

BRIEF DESCRIPTION OF THE DRAWINGS

The invention is further described with reference to the accompanying drawings in which:

FIG. 5 is a side elevational view of the rotary connector embodiment of the invention, illustrating the male and female connector members in a disengaged position;

FIG. 6 is an end elevational view of the inner end of the female connector member of the connector assembly in FIG. 5;

FIG. 7 is a partial side elevation in cross section illustrating a preferred seal configuration;

FIG. 8 is an end elevational view of the seals shown in FIG. 7; and

FIG. 9 is a side elevational view of an embodiment of the invention employing sliding male and female connector members.

DETAILED DESCRIPTION OF THE INVENTION

Figure 1:
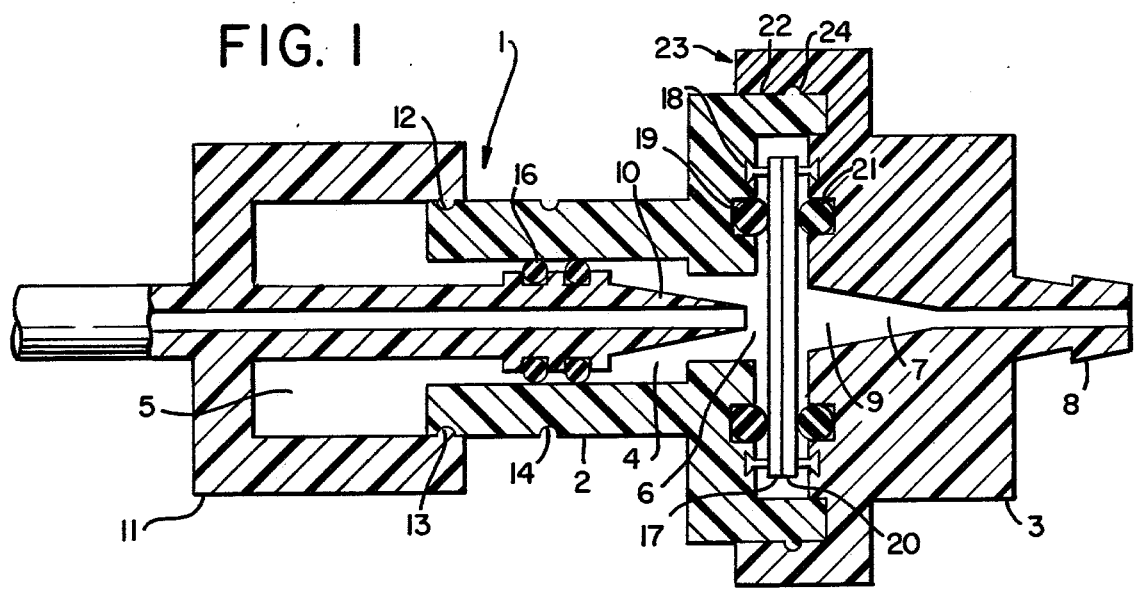
FIG. 1 is a plan view of an embodiment of the invention employing a rectangular sterile connector assembly.
Figure 2:
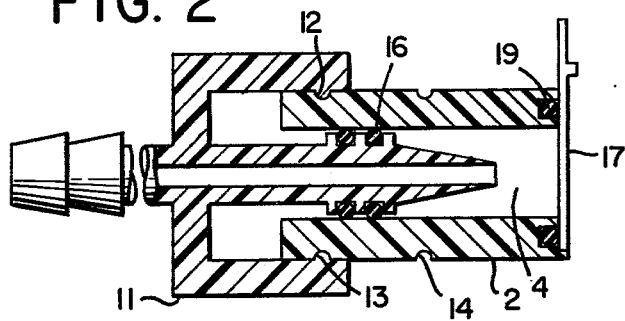
FIG. 2 is a side elevational view of the male connector member of the connector assembly of FIG. 1 having a male luer fitting section positioned therein.

The sterile connector of the invention achieves a desirable combination of convenience of operation and enhanced protection against contamination during engagement and use. The invention utilizes compressible seals and practical shield plates to maintain the sterility of the connector during the intermediate exposure of conduits in the connector members through which luer fittings may readily be engaged to insure the maintenance of sterility. Upon such luer fitting engagement, the seals provide an added assurance against contamination without, at any time, coming into contact with the blood or other fluid passing through the connectors. The regulatory requirements pertaining to the seal material are greatly simplified, therefore, as compared with the requirements for such seals as might be employed in connector assemblies in which such seals would come in contact with said blood or other fluids passing therethrough. Other features of the invention will be indicated with reference to the drawings.

One embodiment of the invention, shown in FIGS. 1–4 of the drawings relates to rectangular connectors having sliding shield plates that separate the sterile compartments of the conduit members from the atmosphere prior to engagement of the luer fittings. The sterile connector, represented generally by the numeral 1, has a male connector member 2 and a female connector member 3 shown in matingly engaged position in FIG. 1. Male member 2 has conduit 4 therein extending from the outer end 5 to the inner end 6 of said member 2. Female connector member 3 has conduit 7 therein forming a female luer fitting section from the outer end 8 to the inner end 9.

Male luer fitting section 10 is positioned within conduit 4 of male connector member 2 from outer end 5 thereof and includes support members 11 movingly secured to connector member 2 as by protrusions 12 adapted for positioning in notch 13, when said male luer fitting section is in its disengaged position and for positioning in notch 14 when said male luer fitting section 10 is moved to its engaged position relative to its companion female luer fitting section 15, i.e. conduit 7, in female connector member 3. O-rings or other flex seals 16 are provided to isolate conduit 4 from the atmosphere at the outer end of connector member 2. When the luer fitting sections are engaged, they can readily be secured, or locked, by a conventional pin in a guide slot arrangement, not shown, as will be readily appreciated by those skilled in the art.

Figure 3:
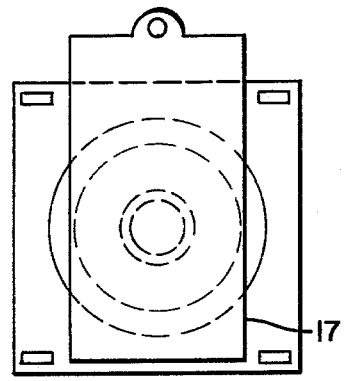
FIG. 3 is an end elevational view of the male connector member taken from the right side of the view depicted in FIG. 2.

As shown particularly in FIG. 3, a sliding shield plate 17 is provided to cover conduit 4 at inner end 6 of connector member 2. Said shield plate 17 is vertically slidable between a lower, closed position, as shown in FIG. 3, and a raised open position in which said shield 17 does not cover said conduit 4, and is slidably secured by a suitable tongue and groove joint within a suitable recessed or grooved frame portion 18 of connector member 2. Positioned intermediate shield plate 17 and inner end 6 of said connector 2 is a compressible seal, i.e. flex seal, 19 shown with a circular shape. Compressible seal 19 may be secured by said recessed frame portion 18 of connector 2 and its related shield plate so that no adhesive materials need be employed with said seals. Likewise, female connector member 3 has a vertically slidable shield plate 20 slidable between a lower, closed position in which said plate covers conduit 7 in female connector member 3 and an upper, open position in which said plate does not cover said conduit 7. Shield plate 20 is slidably secured within a suitable recessed support frame portion 18a of connector member 3 with a suitable tongue and groove joint, with a compressible seal, i.e. flex seal, 21 positioned intermediate said shield plate 20 and the inner end 9 of female connector member 3 and secured by said frame and the shield plate. Shield plate 20 on female connector member 3 and shield plate 17 on male connector member 2 are thus in contacting position when connector members 2 and 3 are in matingly engaged position so that said plates 17 and 20 can be slid simultaneously to uncover the conduits in their respective connector members.

Figure 4:
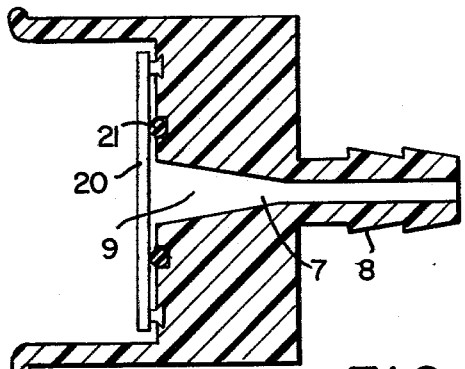
FIG. 4 is a side elevational view of the female connector member of the assembly of FIG. 1 having a conduit therein forming a companion female luer fitting section.

The male and female connector members 2 and 3 each have an extended side portion, e.g. side portions 22 and 23, respectively, having a mating notch and protusion, generally represented in FIG. 1 by the numeral 24, for locking the male and female connector members together. Said side portion 23 of female connector member 3, as illustrated in FIG. 4, represents a variation of the FIG. 1 locking arrangement with said side portion 23 in FIG. 4 shown with protrusions 24 for locking in companion notches in the corresponding side portion of male connector member 2.

Upon securing of the male and female connector members with the inner end 6 of male connector member 2 in matingly engaged position with inner end 9 of female connector member 3, as shown in FIG. 1, conduits 4 and 7 in said members are in alignment so as to permit communication therebetween. With shield plates 17 and 20 in their closed position, however, the shield plates serve to isolate said conduits from the atmosphere at inner ends 6 and 9 of connector members 2 and 3, respectively, and to preclude communication therebetween. As the shield plates are slid vertically upward together to their open position, said conduits are uncovered at the inner end of said connector members. Male luer fitting section 10 can then be moved from its disengaged position to its engaged position, thereby becoming engaged and securely locked with female luer fitting section 15 that is positioned in matingly engagable position in female connector member 3.

As the shield plates are slid together from their closed to their open position, the elastomeric compressible seals 19 and 21 are released and expand outward to contact one another behind the trailing bottom, i.e. edges of the sliding plates. The seals upon such contact form a seal-line that advances as the plates are moved, preventing the sterile compartments within connector members 2 and 3 from being exposed to the atmosphere. Upon engagement of the luer fitting sections after such movement of the shield plates, the seals provide an added assurance against contamination without, however, being exposed to contact with the blood or other fluid passing through the engaged and locked luer fitting within the sterile connector.

The elastomeric compressible seals can be employed in any desired shape, as for example a circular or rectangular form, with a solid cross-sectional form, an X-form cross section forming lip seals upon contact or any other convenient cross-sectional configuration. Flex rings of doughnut shape may be employed to obtain larger seal surface areas. While such seals having holes therein in alignment with the conduit in the connector member to which said seals are secured may readily be employed, it has been found advantageous to employ flex rings, e.g. rectangular flex rings, having a cut therein, as in the form of a slit or a cross-cut in lieu of a hole in such seals. Such a cut allows the male luer fitting section to penetrate through for engagement on the female side and, in addition, acts as a diaphragm that prevents leakage under vacuum or pressure as the shield plates are being moved to their open position.

FIGS. 5 and 6 illustrate an embodiment of the invention in which rotary connector members are employed. Although a generally rectangular connector as shown in FIGS. 1-4 is satisfactory, the size of the connectors is unnecessarily large and their relatively sharp edges may, unless care is taken, damage blood bags upon contact, especially during centrifugation operations. In addition, such a design does not lend itself to maximizing the seal surface area and thus enhancing and rendering more reliable the sealing action achieved. For these reasons, a rotary connector is provided and is represented generally, in FIG. 5, by the numeral 25. Male connector member 26 and female connector member 27 are both of circular form and have circular shaped elastomeric compressible seals 28 and 29, respectively, at the facing, inside ends of said members in matingly engagable position. Circular seals 28 and 29 are each covered by preferably thin shield or disc plates 30 and 31 respectively, that are secured to the respective connector members and are capable of being rotated and/or slid on the seal surfaces of said seals between closed and open positions. In FIG. 6, the inner end portions of a connector member is shown with the shield plate in its closed position covering the hole 32 in the circular seal, i.e. hole 33 in seal 28 and hole 34 in seal 29 of FIG. 5. As shown, said holes are eccentrically located in alignment with conduit 35 in male connector member 26 and with conduit 36 in female connector member 27. Said conduit 36 comprises a female luer fitting section that is a companion to the male luer fitting section positioned in conduit 35. As shield plates 30 and 31 are rotated or slid from their closed position to their open position to uncover holes 30 and 31, compressible seals 28 and 29 are released, expand and contact one another to form a seal-line behind the trailing edge of said plates. As in the rectangular connectors discussed above, the seal-line advances as the plates are moved, thereby preserving the sterile compartments within connector members 26 and 27 from exposure to the atmosphere. Male luer fitting section 37 is movably secured within conduit 35 of male connector member 26, as by support sections 38, with O-rings 39 serving to isolate the end of conduit 35 opposite that covered by shield plate 30 from the atmosphere. Any suitable locking mechanism, such as a pin and groove, or a press fit as by locking mechanism section 30a of shield 30, or protrusions and grooves as in the embodiment of FIG. 1, can be used to lock connector members 26 and 27 together.

In operation of said rotary connector, said connector members are brought together and locked with the inner end of said members covered by said shield plates in matingly engagable position with the holes in the seals and the conduits in the seals and the conduits in said connector members in alignment. The exposed or uncovered portions of seals 28 and 29, as shown in FIG. 6, are adapted to make surface-to-surface contact in this position. The shield plates 30 and 31 are then rotated simultaneously to uncover said holes, enabling male luer fitting section 37 to be moved from its disengaged position to its engaged position in which it passes through said holes 30 and 31 for engagement and secure locking with its companion female luer fitting section, i.e. conduit 36, within connector member 27. The portions of the compressible seals that were under the shield plates prior to rotation of the shields are maintained sterile because no contact with air occurs during the engagement of the connector assembly.

The rotary connector embodiment allows a considerably larger seal area to be utilized than in the rectangular or square connector embodiment and eliminates the necessity for removal of any parts such as the slidable shield plates of the rectangular embodiment as shown above. Thus, the shield plates may be conveniently slid or pivoted so as to expose the hole in the seals intermediate between the inner end portions of the connector members and said covering shield plates. Eccentrically positioned pivot pins can conveniently be employed to facilitate pivoting of the shield plates from their closed to their open position.

It has been found particularly advantageous to utilize, in all of the embodiments of the invention, the seal configuration as shown in FIGS. 7 and 8, in which the compressible seals 40 and 41 do not have open holes therein for the passage of the luer fitting, but have cavities 42 and 43, respectively. Each cavity forms a thin membrane section, i.e. membrane sections 44 and 45, respectively, that is in alignment with the conduit in the related male or female collector member but that is recessed from the sealing surface of the seal. The membrane sections may have cuts, such as slit 46 as shown in FIG. 8. The seals as shown in FIGS. 7 and 8, made of soft elastomeric materials, such as silicone products, readily maintain vacuum as the shields are rotated and the cuts in the membranes do not introduce any undue resistance to penetration by the male luer fitting section. By employing recessed seal membranes, said membranes do not, at any time, come in contact with the edge of the shields and thus avoid surface wiping as the shields are rotated or otherwise moved to their open position and wipe the surfaces of the seals. As indicated above, the recessed membranes maintain the sealing that is needed and allow the male luer fitting section to penetrate through the cross-cut, slit or other cut in the membranes and couple with the female luer fitting section. The possibility of edge contamination touching the luer fittings is thus eliminated. The surfaces of the seals wiped by the movable shield plates in any of the embodiments of the invention can be treated so as to have a desirably low frictional surface such as by applying a thin coating of RTV, i.e. room temperature valcanizing, silicone rubber to said seal surfaces, sprinkling muscovite mica powder thereon and heating the thus-treated seals in an oven, if desired, to accelerate vulcanization, so as to permanently cure said coating on the seal surfaces.

FIG. 9 illustrates a further embodiment of the invention in which means are provided to position male and female connector members 48 and 49 in a non-matingly engaged position as shown with the outer surfaces of the respective compressible seals 50 and 51 essentially in the same plane. As one connector member is slid with respect to the other within a suitable supporting frame, not shown, so that the connectors 48 and 49 move to a matingly engaged position, any convenient means, such as grooves and pins in the connectors, may be employed to cause the shield plates 52 and 53, respectively, to be slid away from the connectors so as to uncover said conduits. It will be appreciated that such sliding action will take place until the conduits 54 and 55 in the respective connectors, are in alignment so that the luer fittings, not shown, may be engaged. In this embodiment, contact between the compressible seals commences once the sliding action starts and, because of the initial alignment of the contacting seal surfaces, minimum resiliency is required. This embodiment lends itself particularly to utilization with small rectangular connectors of the type described above. Suitable materials for the connector body members include, but are not limited to, polypropylene, polycarbanate, polysulfone, polyethylene and the like. The compressible seals likewise can be made of any suitable, commercially available seal materials, such as the silicone rubber referred to above. The blood or fluid passages, including the luer fittings, must, of course, be made of a medical grade, hemo-compatible material. As will be appreciated by those skilled in the art, a conventional 10° or other convenient taper angle may be employed for the luer fittings. The sterile connectors as disclosed herein employ shield plates that are to be distinguished from shield films, but that are not required necessarily to be rigid in nature. The shield plates, which may be constructed of the same material as the connector body members or may be constructed of metal or other suitable material, are preferably relatively thin, for example on the order of about 0.010–0.020". As such, the shield plates are commonly of a semi-rigid nature, but with sufficient strength to avoid the disadvantages associated with film-type shields.

In providing practical and highly effective sterile connector embodiments, the invention provides a major advance in the art. The sterile connector of the invention is readily capable of withstanding the pressures and/or vacuum transmitted to the connector when attached to a blood bag or other article, directly or through an intermediate tubing, during autoclaving of the article for sterilization or, for example, during centrifuging of the blood bag or other article. The sterile connector of the invention is likewise capable of withstanding high flow rates that, when flex seals alone are employed, can cause leakage to occur around the seals. In the present invention, the securely locked luer fitting can withstand such high line pressures, with the seals providing an additional assurance against such leaks. The shield plates provide an enhanced assurance against rupturing and contamination as compared to a film-like shield. In production, the connectors of the invention have desirable simplicity and do not require adhesion of the compressible interface of the seals. The flex seals provide assurance against contamination during intermediate operation prior to luer fitting engagement and thereafter, without contact with the blood or other fluid passing through the connector, provide added assurance against contamination. The sterile connectors of the invention, in addition, do not require an outside external power source for sterilization. The invention thus satisfied the requirements of the art for a sterile connector having simplified design and operation together with enhanced protection against contamination. The invention achieves these desirable features in a manner not only satisfying present sterile connector requirements but enhancing the prospects for eventual extension of the 24 hour post thaw period in blood freezing and washing. For all of these reasons, the invention contributes in a highly significant manner to the sterile connector art and provides a practical sterile connector of enhanced sterility protection for blood and other fluid processing systems.

What is claimed is:

1. A sterile connector having enhanced sterility protection and simplified operating capability comprising:
   (a) a male connector member having a conduit extending therethrough, said conduit adapted to position a male luer fitting section therein;
   (b) a female connector member having a conduit extending therethrough, said conduit comprising a companion female luer fitting section;
   (c) means to secure said male connector member to said female connector member in matingly engaged position with the conduits in said members in alignment so as to permit communication therebetween;
   (d) shield plates positionable so as to cover and isolate the conduits in said male and female connector members from the atmosphere, said shields being positioned intermediate the male and female connector members when said members are in said matingly engaged position, with one shield plate being affixed to the male connector member and the other shield plate being affixed to the female connector member, said shield plates being movable so as to uncover the respective conduits in said male and female connector members;
   (e) a male luer fitting section positioned in the conduit of the male connector member, said section being adapted to isolate the end of the male connector member conduit opposite that covered by said male member shield plate from the atmosphere, said male luer fitting section being movable so as to engage and lock with female luer fitting section when said shield plates are positioned so as to uncover said conduits in the male and female connector members; and
   (f) compressible seals positioned intermediate said male and female connector members and their respective shield plates, said seals being adapted to maintain isolation of said conduits from the atmosphere as said shield plates are moved so as to uncover said conduits, said seals expanding and contacting one another behind the trailing edge of said shield plates, thus forming a seal-line that advances as the shield plates are moved and preventing the sterile conduits within said male and female connected members from being exposed to the atmosphere, whereby said luer fittings may be readily and effectively engaged and locked in a sterile environment preserved by the seal-line of said compressible seals during the convenient moving of said shield plates to expose the conduit openings through which said luer fittings are engaged, said seals providing an added assurance against contamination of fluid passing through the engaged luer fitting within the connector without exposure of said seals to contact by said fluid passing through the connector.

2. The sterile connector of claim 1 in which said shield plates are slidable plates capable of being slid out to expose said conduits at the inner ends of said connector members.

3. The sterile connector of claim 2 and including a frame on each connector member, said slidable plates being seated in said frame when in the closed position and being slidable upward to the open position with said compressible seals being released so as to form said seal-line as the plates are slid upward, thus preventing the exposure of the sterile conduit area within the connector members to outside air.

4. The sterile connector of claim 1 in which said compressible seals comprise rectangular flex seals having a cut therein facilitating the penetration of the male luer section therethrough for engagement with the companion female luer section on the other side of said connector.

5. The sterile connector of claim 3 in which said compressible seals comprise rectangular flex seals having a cut therein facilitating the penetration of the male luer section therethrough for engagement with the female luer section on the other side of said connector.

6. The sterile connector of claim 1 in which said compressible seals comprise flex seals of circular shape.

7. The sterile connector of claim 1 in which said compressible seals comprise flex seals having a doughnut configuration.

8. The sterile connector of claim 1 in which said compressible seals comprise flex seals having an X-form cross-section, thereby forming lip seals upon contact.

9. The sterile connector of claim 1 in which said male and female connector members are of rectangular configuration.

10. The sterile connector of claim 1 in which said male and female connector members are of rectangular configuration.

11. The sterile connector of claim 1 in which said male and female connector members are of circular configuration and said compressible seals comprise flex seals of circular shape.

12. The sterile connector of claim 11 in which said shield plates comprise rotatable plates capable of rotation between a closed position in which said plates cover the conduits in said connector members and an open position in which said plates expose said conduits for engagement of said luer fittings.

13. The sterile connector of claim 12 in which said conduits are eccentrically positioned, said circular flex seals having openings therein in alignment with said conduits.

14. The sterile connector of claim 12 in which said flex seals have cavities therein in alignment with said conduits, said cavities forming thin membrane sections in said seals, said membrane sections being penetrable by said male luer fitting section and being recessed from the sealing surface of said seals, thereby avoiding contact with the edge of the shield and the sealing surface wiping that occurs as the shield plates are moved to uncover said conduits.

15. The sterile connector of claim 14 in which said membrane sections have cuts therein facilitating said penetration of the male luer fitting section.

16. The sterile connector of claim 14 in which said cavities are eccentrically positioned, facilitating rotation of said shield plates between said closed and open positions.

17. The sterile connector of claim 1 and including means to position said male and female connector members in a non-matingly engaged position with the outer surfaces of said compressible seals essentially in the same plane and means for causing said shield plates to slide away from said connector members as one connector is slid with respect to the other to said matingly engaged position.

18. The sterile connector of claim 17 in which said male and female connector members are of rectangular configuration.

19. The sterile connector of claim 18 in which said compressible seals comprise flex seals of circular shape.

20. The sterile connector of claim 18 in which said compressible seals comprise flex seals having cavities therein in alignment with said conduits, said cavities forming thin membrane sections in said seals, said membrane sections being penetrable by said male luer fitting section and being recessed from the sealing surface of said seals, thereby avoiding contact with the edges of the shield plates and the sealing surface wiping that occurs as said shield plates are moved to uncover said conduits.

21. The sterile connector of claim 20 in which said membrane sections have cuts therein facilitating said penetration of the male luer fitting section.

22. The sterile connector of claim 18 in which said compressible seals comprise flex seals having a doughnut configuration.

23. The sterile connector of claim 1 in which said compressible seals comprise flex rings having cavities therein in alignment with said conduits, said cavities forming thin membrane sections in said seals, said membrane sections being penetrable by said male luer fitting section and being recessed from the sealing surface of said seals, thereby avoiding contact with the edges of the shield plates and the sealing surface wiping that occurs as said shield plates are moved to uncover said conduits.

24. The sterile connector of claim 10 on which said compressible seals comprise flex seals having cavities therein in alignment with said conduits, said cavities forming thin membrane sections in said seals, said membrane sections being penetrable by said male luer fitting section and being recessed from the sealing surface of said seals, thereby avoiding contact with the edges of the shield plates and the sealing surface wiping that occurs as said shield plates are moved to uncover said conduits.

* * * * *